United States Patent [19]

Yeh et al.

[11] Patent Number: 5,032,384

[45] Date of Patent: Jul. 16, 1991

[54] COMPOSITIONS AND METHOD FOR THE TREATMENT OF DISEASE

[75] Inventors: Kuo-Chen Yeh, Westfield, N.J.; Frank J. Sena, Brooklyn, N.Y.; Michael C. Alfano, Franklin Lakes, N.J.

[73] Assignee: Block Drug Company, Inc., Jersey City, N.J.

[21] Appl. No.: 302,210

[22] Filed: Jan. 27, 1989

[51] Int. Cl.$^5$ .................... A61K 7/16; A61K 9/06; A61K 9/70; A61L 15/03
[52] U.S. Cl. ............................ 424/49; 424/435; 424/443; 514/900; 514/902
[58] Field of Search .................. 424/49–58, 424/443, 435; 514/900, 902

[56] References Cited

U.S. PATENT DOCUMENTS

| | | | |
|---|---|---|---|
| 4,411,885 | 10/1983 | Barels et al. | |
| 4,569,837 | 2/1986 | Suzuki et al. | 424/435 |
| 4,627,850 | 12/1986 | Deters et al. | 604/892.1 |
| 4,647,586 | 3/1987 | Mizushima et al. | 514/532 |
| 4,666,701 | 5/1987 | Horrubin et al. | 424/10 |
| 4,684,632 | 8/1987 | Schulz et al. | 514/78 |
| 4,755,544 | 7/1988 | Makino et al. | 424/468 |
| 4,772,470 | 9/1988 | Inove et al. | 424/435 |
| 4,778,799 | 10/1988 | Tibes et al. | 514/277 |
| 4,814,176 | 3/1989 | Makino et al. | 424/457 |
| 4,837,214 | 6/1989 | Tanaka et al. | 514/179 |
| 4,847,069 | 7/1989 | Bissett et al. | 424/47 |
| 4,847,071 | 7/1989 | Bissett et al. | 424/59 |
| 4,847,072 | 7/1989 | Bissett et al. | 424/59 |
| 4,869,897 | 9/1989 | Chatterjee et al. | 424/47 |
| 4,900,554 | 2/1990 | Yanagibashi et al. | 424/448 |
| 4,906,670 | 3/1990 | Higashi et al. | 514/773 |
| 4,917,886 | 4/1990 | Asche et al. | 424/81 |
| 4,933,182 | 6/1990 | Higashi et al. | 424/435 |
| 4,939,135 | 7/1990 | Robertson et al. | 514/179 |
| 4,946,671 | 8/1990 | Bissett et al. | 424/59 |
| 4,946,870 | 8/1990 | Partain | 514/177 |
| 4,954,332 | 9/1990 | Bissett et al. | 424/59 |

FOREIGN PATENT DOCUMENTS 380367 8/1990 European Pat. Off. .

OTHER PUBLICATIONS

Offenbacher et al., Chem. Abstr. 112(9):70787s (1990), of Agents Actions 29(314):232-8 (1990).
Bertolini et al., GA.97:197213d (1982).
Barels et al., CA.100:25956n (1984).
Julius C.A.102:226058m(1985), Hall et al., CA.109:196923q(1988), Herman et al. GA.111:126644s(1989).
Nasyrov et al. GA.102:142897w (1985), Haneletal CA.98:11189t (1983), Yogel et al. CA.104:199759y (1986).
Mouney et al., CA.88.94686v (1978).
Meisner, GA.110:128652w (1989).
Fahim et al., CA.96:149000q (1982).
Loesche, CA.104:193211s (1986).
"Vitamin E Enhances the Activity of Non-Steroidal Anti-Inflammatory Durgs", by A. Bertolini et al., Rivistadi Framacologia E Terapia 13(1): 27-34, 1982.
"The Effect of a Topical Non-Steroidal Anti-Inflammatory Drug on the Development of Experimental Gingivitis in Man", by P. A. Heasman et al., J. Clin. Periodontol, 1989, 16:353-358.
Patent Abstracts of Japan, vol. 8, No. 241 (C-250)(1678), 6 Nov. 1984, & JP-A-59 122422 (Toukou Yakuhin Kogyo K.K.), 14.07.84.

*Primary Examiner*—Shep K. Rose
*Attorney, Agent, or Firm*—Ostrolenk, Faber, Gerb & Soffen

[57] ABSTRACT

Synergistic compositions comprising an antioxidant and an arylpropionic, non-steroidal anti-imflammatory drug used to treat certain diseases are disclosed. The compositions inhibit production of arachidonic acid cascade end-products which have been implicated as causes of tissue-destruction in periodontal disease. The compositions are administered in combination with a carrier, which may be a mucosal-tenacious polymer selected from the groups of semi-solid pastes, gels, ointments, liquids or films.

12 Claims, No Drawings

COMPOSITIONS AND METHOD FOR THE TREATMENT OF DISEASE

BACKGROUND OF THE INVENTION

Periodontal disease is an inflammatory disorder of the supporting tissue of teeth. Without control, chronic inflammatory condition associated with periodontal disease will destroy tissue supporting teeth and eventually result in teeth loss.

Attempts have been made to alleviate periodontal disease using chemical agents. For example, U.S Pat. No. 4,789,662 to Thomas-Leurquin et al. discloses a pharmaceutical composition including collagen and a chlorhexidine antiseptic and anti-inflammatory substance. However, the traditional mode of prevention and treatment of periodontal disease has centered on maintaining good oral hygiene. This consists of, among other things, removal of dental plaque which is considered to be the etiological cause of dental caries and periodontal disease. Dental plaque consists of microbial masses which deliver a stream of enzymes, endotoxins and exotoxins onto gingival and marginal periodontal tissue leading to inflammation. The resulting inflammatory response triggers a series of catabolic processes. Specifically, as tissue reacts to protect itself from these toxic assaults, complex changes occur in the immune system in the function of osteoclasts, in the activity of lymphocytes in the blood streams, and in other bodily defenses. These changes and complement activation lead to increased prostaglandin formation at the inflammation site.

Prostaglandin, and related compounds, are principally formed by body cells at the site of tissue injury by a process known as arachidonic acid cascade This process occurs when essential fatty acids, especially linoleic acid, are enzymatically converted into arachidonic acid, which in turn is further metabolized through either the cyclooxygenase or lipoxygenase pathways to prostaglandins (PGS).

Prostaglandins, particularly prostaglandin-$E_2$ ($PGE_2$), have been implicated as components of the inflammatory reaction. Goodson et al., Prostaglandins, 6, 81-85 (1984) and El Attar et al., J. Periodontal, 52, 16-19 (1981) demonstrated that $PGE_2$ levels are elevated in inflamed gingiva when compared to normal gingiva. Offenbacher et al., J. Periodont. Res., 21, 101-112 (1986) demonstrated that extremely high levels of $PGE_2$ are present at periodontal sites of active attachment loss and low at sites which are in remission, i.e. there is no longitudinal attachment loss. The $PGE_2$ level in diseased tissue approximates 1 uM (Offenbacher et al., J. Periodon. Res. 19, 1-13 (1984)) which is a pharmacologically active concentration when tested in various model systems to induce vasodilation, bone resorption and other pro-inflammatory responses.

Despite this evidence regarding the key role of $PGE_2$ in the pathogenesis of periodontal disease, there has been substantially little appreciation of the use of drugs which inhibit $PGE_2$ synthesis in an attempt to retard or prevent periodontal tissue destruction.

SUMMARY OF THE INVENTION

Accordingly, it is an object of the invention to provide new compositions and a method which inhibit prostaglandin formation and are therefore useful for the treatment of periodontal disease.

These and other objectives are achieved by providing a synergistic composition which comprises an antioxidant in combination with an arylpropionic, non-steroidal anti-inflammatory drug (NSAID) The antioxidant is preferably alpha-tocopherol, ascorbic acid or pharmaceutically acceptable salts thereof, or Vitamin A and its precursors including beta-carotene. The arylpropionic NSAID is preferably an alpha-arylproprionic NSAID, most preferably, ibuprofen, flurbiprofen, ketoprofen, fenoprofen or naproxen. The antioxidant and NSAID are combined with a pharmaceutically acceptable carrier The compositions are preferably formed into a laminate occlusive dressing, tablet capsule, pill, solution, gel suspension, or the like. In these types of formulations, antioxidant is preferably present in the composition in the range from about 0.01 to 10% by weight, and most preferably 0.03 to 2% by weight. NSAID is preferably present in the composition in the range from about 0.01 to 10% by weight and most preferably 0.01 to 2% by weight. Alternately, the composition may be compounded in a mucosal-tenacious polymer, preferably a water soluble or water dispersible karaya gum, ethylene oxide polymer, sodium carboxymethylcellulose or lower alkyl vinyl ether-maleic acid anhydride copolymer. The polymer, having the therapeutically effective composition therein, can be applied directly to the gingival tissues.

DETAILED DESCRIPTION OF THE INVENTION

Antioxidants reduce the oxidation of arachidonic acid by competing for enzymatically formed oxygen radicals during arachidonic acid cascade. The result of this competition is a decrease of prostaglandin synthesis and a concomitant decrease in plaque-induced gingival inflammation in addition to the tissue destruction which is associated therewith. Non-steroidal anti-inflammatory drugs (NSAID) treat inflammation, but have limited effectiveness in fighting the underlying disease origins of the inflammation.

According to the present invention, it has been discovered that the combination of one or more antioxidants and one or more arylpropionic, non-steroidal anti-inflammatory drugs produces a synergistic result in the treatment of inflammatory diseases, and in particular periodontal disease, by the reduction or prophylaxis of prostaglandin formation at the inflammation site. Preferably, the antioxidants are alpha-tocopherol, ascorbic acid or pharmaceutically acceptable salts thereof, or Vitamin A and its precursors including beta-carotene. Other antioxidants may be utilized in the present invention The NSAID is preferably an arylpropionic compound, preferably an alpha-arylproprionic acid or pharmaceutically acceptable salts thereof. Such compounds may be represented by the following formula

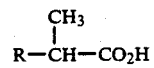

where R is an aromatic group and the compound possesses anti-inflammatory properties. Most preferably, the alpha-arylpropionic acid is ibuprofen, flurbiprofen, ketoprofen, fenoprofen, or naproxen.

In the determination of the synergistic activity of the compositions according to the present invention, the following in vitro testing was affected. A large pool of inflamed human gingival tissue was obtained from patients with periodontitis who were undergoing routine periodontal surgery. The tissues were immediately stored in liquid nitrogen prior to use or were used fresh. The assay of cyclooxygenase products was performed as a modification of the assay of El Attar et al., J. Periodon. Res., 21, 169-176 (1986). Pooled tissue was weighed and homogenized at 0°-4° C. with a Polytron ® (Brinkman) homogenizer in a 0.2 M TRIS buffer, pH 8.0, at a final concentration of 20 mg/ml. After centrifugation for 10 minutes at $1200 \times g$, the supernatant was divided into 3 ml aliquots for incubation in the presence or absence of a test compound.

The test compounds were tested in triplicate over a concentration range of $10^{-8}$ to $10^{-14}$ M. For example, alpha-tocopherol from $10^{-12}$ to $10^{--}$M was coupled with ketoprofen from $10^{-8}$ to $10^{-14}$ M range in a total of $3 \times 7$ matrix combinations in order to determine the synergistic effect as well as the $IC_{50}$ (dosage concentration to reach 50% inhibition) of the combination.

Prostanoids were extracted as described by Powell, Methods in Eng., 86, 467 (1982) using a Sep-Pak-$C_{18}$ cartridge from Waters Associates. The Sep-Pak was prepared by the sequential elution of 20 milliliters of ethanol and 20 milliliters of water. The sample was then adjusted to 15% ethanol, pH 3.0, with acetic acid and applied to the column. The column was eluted with 20 ml of 15% ethanol, pH 3.0, 20 ml of petroleum ether and then the prostaglandin Tx (thromboxane) was eluted with 10 ml of methyl formate. Thereafter, the methyl formate was evaporated to dryness with nitrogen and reconstituted in 32% acrylonitrile (high pressure liquid chromatography buffer).

Previous experience had revealed that the recovery was greater than 92% from $PGE_2$, $PGI_2$ (as 6KFl), $TxA_2$ (as $TxB_2$) and $PGF_2$. These are readily separated and quantified using a $4.6 \times 100$ nm RP-18 Spheri-5u column from Brownle Labs. A Flow-One radioactivity monitor simultaneously measured radioactivity while monitoring elution at 192 nanometers.

The net incorporation of the $14_C$ arachidonate was measured in the absence of the test substance in order to determine the maximum activity of the cyclooxygenase cascade.

The following Table 1 indicates the percent of control (maximum) $PGE_2$ synthesis as a function of alpha-tocopherol and ketoprofen concentration.

TABLE 1

| | Percent of $PGE_2$ Synthesis In Presence of Ketoprofen and Alpha-Tocopherol | | | | | | |
|---|---|---|---|---|---|---|---|
| Alpha-tocopherol Concentration (M) | Ketoprofen Concentration (M) | | | | | | |
| | $10^{-14}$ | $10^{-13}$ | $10^{-12}$ | $10^{-11}$ | $10^{-10}$ | $10^{-9}$ | $10^{-8}$ |
| At $10^{-14}$M | 102 | 129 | 116 | 131 | 112 | 75 | 97 |
| At $10^{-13}$M | 105 | 68 | 101 | 82 | 62 | 61 | 36 |
| At $10^{-12}$M | 66 | 68 | 41 | 62 | 48 | 51 | 49 |

As can be seen from Table 1, the exemplary composition of alpha-tocopherol and ketoprofen in combination resulted in a synergistic effect in the inhibition of $PGE_2$. Specifically, alpha-tocopherol lowered the $IC_{50}$ value of ketoprofen and ketoprofen lowered the $IC_{50}$ value of alpha-tocopherol.

In carrying out the method of the present invention, the antioxidant and arylpropionic, NSAID composition can be combined with a pharmaceutically acceptable carrier and administered orally, topically or bucally to the patient in need of treatment. Suitable forms of administration of the composition are forms such as laminate occlusive dressings, tablets, capsules, pills, solutions, gels, suspensions and the like.

The compositions of the present invention include an effective periodontal disease reducing amount of the antioxidant and NSAID in combination with the pharmaceutically acceptable carrier. The amount of active ingredients in the composition are about 0.01 to 10% by weight for the antioxidant and about 0.01 to 10% by weight for the arylpropionic, NSAID. The preferred weight % are about 0.03 to 2.0% for the antioxidant and about 0.01 to about 2.0% for the arylpropionic, NSAID. The carriers may include other materials such as lubricants, e.g., stearic acid or magnesium stearate, fillers such as lactose, sucrose and corn starch, desegregating agents such as algeic acid, surface active agents for use in injectable solutions or suspensions, and the like.

According to another embodiment of the invention, the synergistic compositions may be compounded into a carrier which has a strong and continuing adherence to the oral gingival mucosa. The carrier may then be applied to gingival tissues for two hours or longer in order to achieve a protracted topical therapeutic effect. Compositions of preferred vehicles which have acceptable properties are described herein as "mucosal-tenacious" and may be created from a variety of water-soluble or water-dispersible polymeric materials combined with other adjuvants.

All such materials used in the vehicle however, must have certain properties in common which are summarized below:

(1) They must be virtually non-toxic systemically.
(2) They must not irritate or damage bodily tissues at the site of the application.
(3) They must be water-soluble or water-dispersible polymeric molecules.
(4) They must be chemically and physically compatible with the synergistic composition.
(5) They must have a strong and persistent adherence to oral mucosal tissues, preferably for a minimum of 2 hours after application to affected tissues.
(6) They must allow the slow diffusion of the synergistic composition from the vehicle so that it can contact and permeate the mucosa at the site of application for protracted periods of time.
(7) They must be readily removable from the site of application by use of mild mechanical abrasion and a non-toxic detergent solution.

The mechanism by which a polymeric material bonds to oral mucosal tissues is complex. It is believed that chemical, physical and mechanical bonds form as permeation of molecules takes place into the irregularly contoured surface of the mucosal substrate. Since all body cells in vertebrate animals carry a net negative surface charge and most polymeric agents carry a net positive charge, an electrostatic bond develops due to coulombic attractions, van der Waal forces, hydrogen bonding and covalent bonding.

There are a number of polymeric agents which can be employed to prepare mucosal-tenacious vehicles with the seven required attributes enumerated above. Among these are natural gums, plant extracts, animal extracts, cellulose derivatives, polyvinyl alcohols, polyvinylpyrrolidone, polycarbophil, polyacrylic acid derivatives, polyacrylamides, ethylene oxide homopolymers, polyethelene-polypropylene copolymers, polyethylenimines and others.

It is important in selecting a composition for the mucosal-tenacious vehicle that it allow the slow diffusion of the synergistic composition from the vehicle and into contact with the gingival tissues so that it can be absorbed into those tissues where it will induce its beneficial effects.

The chemical structures of the polymeric agent selected for use in the mucosal-tenacious vehicle of this invention are not nearly as important as their physical properties and ability to satisfy the seven conditions set forth above. However, a large number of materials can be selected which do satisfy these criteria if properly compounded at suitable concentrations into a vehicle such as a semi-solid paste, gel, liquid, ointment or film.

Among such agents are a number of natural hydrophilic polymeric agents, which are enumerated below:
(1) Agar, which is a hydrophilic colloid extracted from certain algae. It is relatively insoluble in cold water but soluble in hot water.
(2) Algin is derived from a brown algae, principally microcystitis pyriera. It is a linear polymer of high molecular weight; it is extracted principally as alginic acid and readily forms water-soluble alkali metal derivatives, amine derivatives and esters, all of which can be used in accordance with the teachings of this invention.
(3) Carageenan is another algae-derived water-soluble polymer and exists principally as the lambda, kappa and iota isomers.
(4) Other water-soluble polymers also derived from marine algae include fucoidan, laminoran and furcellaran.
(5) Gum arabic, also commonly called gum acacia, is the dried, gummy exudate of the acacia tree, indigenous to Africa, India, Central American and Southwest North America. It readily forms coacervates with gelatin.
(6) Gum ghatti is another tree exudate which has a higher viscosity in aqueous solutions than gum arabic.
(7) Gum karaya is a tree exudate with a high potential for water absorption and a relatively low pH. At concentrations of 5%-20%, it is a strong wet adhesive.
(8) Gum tragacanth is widely used in food processing and is obtained from a perennial shrub found in the Near East.
(9) Guar gum is obtained from the guar plant in India and Pakistan and forms viscous, colloidal dispersions in water.
(10) Locust bean gum is derived from the fruit of the carob tree, an evergreen found principally in Southern Europe.
(11) Other natural gums derived from the fruit of the carob tree, an evergreen found principally in southern Europe.
(12) Pectin is a general term for a group of water-soluble and water-dispersible polysacharides present in the cell walls of all plant tissues.
(13) A relatively recent type of water-soluble, natural polymer is that produced as an extracellular polysaccharide by bacteria or fungi. Included among these are xanthan gum, polysaccharide Y-1401, scleroglucan and various dextrans.

There are also some starch derivatives which meet many of the criteria outlined for a mucosal-tenacious, water-soluble or water-dispersible polymer above, but are not usable in this invention because of their susceptibility to amylolytic degradation from the enzyme ptyalin found in saliva.

In addition to the natural hydrophilic polymers, the following synthetic polymers may also be used:
1. Chemical modification of cellulose provides many derivatives which are useful within the teachings of this invention. Among these are methyl cellulose, sodium carboxymethylcellulose, hydroxypropylmethylcellulose, hydroxypropylethylcellulose, hydroxypropyl cellulose; and ethylhydroxyethyl cellulose. These agents can be prepared in a wide range of solubility and viscosity ranges.
2. Polyvinyl alcohol is produced by the alcoholysis of polyvinyl acetate and can be made in a number of molecular weights, water-solubility ranges and viscosity ranges.
3. Polyvinylpyrrolidone is a homopolymer of N-vinylpyrrolidone with a high level of water solubility and pronounced viscosity-building properties.
4 Polyacrylic acid derivates can be used directly but more often are used with other copolymers; an important polyacrylic acid copolymer is polycarbophil.
5. Particularly useful materials are the partial calcium/sodium salts of lower alkyl vinyl-maleic acid anhydride copolymers, sold commercially as "Gantrez" and "Ucarset".
6. Polyacrylamide is a polymer of acrylamide and can be polymerized by a variety of synthetic approaches.
7. Ethylene oxide polymers of very high molecular weight are commercially sold by the Union Carbide Co. as water-soluble resins ("Polyox"). They range in molecular weight from a few hundred thousand to five million or more. The higher molecular weight derivatives have extraordinary viscosity-building effects in water and other solvents, as well as pronounced mucosal-tenacity.
8. Polyethylenimines are produced from the monomer ethylenimine in the presence of an acid catalyst. They are of special interest for adherent formulations because of their tendency to form strong electrostatic bonds.

It is also possible to use at least one material of animal origin:
1. Gelatin is a partially hydrolized protein derived from the skin, connective tissues and bones of mammalian animals; that derived by acid treatment is Type A and that from alkali treatment is Type B.

These various polymeric materials herein described are illustrative of the many agents from which a composition can be compounded into useful mucosal-tenacious carriers. They may be used singly or in combination, in a wide range of concentrations, and in the presence of many other agents intended to control rates of water absorption and swelling, ingredients to enhance tissue penetration, various fillers, buffers, sweeteners, flavors, bodying agents and other pharmaceutical necessities.

Generally, such compositions include about 0.01 to about 10 parts antioxidant, about 0.01 to 10 parts arylpropionic, NSAID, and about 20 to about 60 parts mucosal-tenacious polymer.

Examples 1-7 below are illustrative of pharmaceutically acceptable carriers with synergistic compositions therein which can be used in accordance with the teachings of the invention.

EXAMPLE 1

| Components | % By Weight |
| --- | --- |
| 1. CMC 7H3SXF (Sodium Carboxymethylcellulose) | 10.0 |
| 2. Polyox (Polyethylene Oxide) | 20.0 |
| 3. Polycarbophil | 10.0 |
| 4. Calcium Oxide | 1.0 |
| 5. Ketoprofen | 1.0 |
| 6. Alpha-tocopherol | 1.0 |
| 7. Polyvinylacetate | 23.0 |
| 8. Triacetin | 34.0 |
| | 100.0 |

Polyvinylacetate and triacetin were pre-mixed in a sigma-blade mixer. CMC 7H3SXF, polyox powder, polycarbophil, calcium oxide and ketoprofen were homogeneously mixed in a Tekmar mixer, followed by the addition of alpha-tocopherol at 1000 rpm Finally, the polyvinylacetate/triacetin pre-mix was added to the mixture, and resulted in a smooth cream-type product.

EXAMPLE 2

| Components | % By Weight |
| --- | --- |
| 1. Mineral Oil | 51.45 |
| 2. CMC 7H3SXF (Sodium Carboxymethylcellulose) | 32.0 |
| 3. Polyox (Polyethylene Oxide) | 13.0 |
| 4. Propylparaben | 0.05 |
| 5. Sodium Monophosphate | 0.10 |
| 6. Flavor (Spray Dried) | 0.40 |
| 7. Ketoprofen | 2.0 |
| 8. Alpha-tocopherol | 1.0 |
| | 100.0 |

Mineral oil was heated to 65° C. ion a Kitchen-Aid Bowl. CMC 7H3SXF, polyox, propylparaben and sodium monophosphate were slowly charged to the bowl and mix-homogeneously for 10–15 minutes. Finally the active agents (alpha-tocopherol and ketoprofen) and flavor were added and mixed thoroughly.

EXAMPLE 3

| Components | % By Weight |
| --- | --- |
| 1. Ethanol | 15.0 |
| 2. Glycerin | 15.0 |
| 3. Polysorbate | 1.0 |
| 4. Sodium Lauryl Sulfate | 0.1 |
| 5. Ketoprofen | 1.0 |
| 6. Alpha-tocopherol | 1.0 |
| 7. Flavor | 0.1 |
| 8. Colorant (FD&C Grade) | 0.005 |
| 9. Water | 66.795 |
| | 100.0 |

Active agents (alpha-tocopherol and ketoprofen) were mixed homogeneously with ethanol in a container. In another container, flavor, glycerin, sodium lauryl sulfate, colorant and polysorbate were mixed together, followed by the addition of water. The ethanol (and active agents) solution was then charged to the aqueous portion and mixed thoroughly.

EXAMPLE 4

| Components | % By Weight |
| --- | --- |
| 1. Ethylene Oxide Homopolymer | 40.0 |
| 2. Polyvinylpyrrolidone | 40.0 |
| 3. Polyethylene Glycol 4000 | 14.9 |
| 4. Glycerin | 1.0 |
| 5. Ketoprofen | 2.0 |
| 6. Alpha-tocopherol | 2.0 |
| 7. Flavor | 0.1 |
| | 100.0 |

The first four ingredients are homogenized into an intimate mixture and warmed to about 40° C. The active agents and flavor were incorporated into the mixture and mixed thoroughly. The final mixture was cooled to about 25° C. and then extruded through stainless steel rollers into a film approximately 2 mm thick.

| Components | % By Weight |
| --- | --- |
| 1. Ketoprofen | 2.0 |
| 2. Alpha-tocopherol | 2.0 |
| 3. Hydrated Silica | 12.0 |
| 4. Sorbitol Solution | 12.0 |
| 5. Glycerin | 12.0 |
| 6. Xanthan Gum | 1.5 |
| 7. Fumed Silica | 2.0 |
| 8. Flavor | 0.5 |
| 9. Propyl Paraben | 0.05 |
| 10. Methyl Paraben | 0.05 |
| 11. Sodium Lauryl Sulfate | 1.5 |
| 12. Water | 54.4 |
| | 100.0 |

In a mixing vessel container fitted with a vacuum system and mixing apparatus, water, active agents, parabens, flavor, sorbitol solution, and silica were charged and mixed thoroughly. In a separate container xanthan gum was charged and mixed in glycerin and then charged to the mixing vessel. It was then mixed for about 10 minutes, detergent was added, and finally mixed under full vacuum for 20-30 minutes.

EXAMPLE 6

| Components | % By Weight |
| --- | --- |
| 1. Lactose | 57.0 |
| 2. Avicel (pH 101) | 33.0 |
| 3. Starch | 4.0 |
| 4. Fumed Silica | 1.0 |
| 5. Stearic Acid | 2.0 |
| 6. Alpha-tocopherol | 2.0 |
| 7. Ketoprofen | 1.0 |
| | 100.0 |

Active ingredients (alpha-tocopherol and ketoprofen) were mixed homogeneously with lactose in a Ribbon mixer followed by the addition of Avicel, starch, fumed silica and finally stearic acid. Manesty equipment was used to produce tablets (average weight: 500 mg.).

EXAMPLE 7

| Components | % By Weight |
| --- | --- |
| 1. Lactose | 80.0 |

-continued

| Components | % By Weight |
|---|---|
| 2. Starch | 17.0 |
| 3. Alpha-tocopherol | 1.0 |
| 4. Ketoprofen | 1.0 |
| 5. Fumed Silica | 1.0 |
| | 100.0 |

Alpha-tocopherol was homogeneously dispersed with lactose in a Ribbon Mixer, followed by ketoprofen, starch and fumed silica. After the powder was homogeneously mixed, it was then filled into hard gelatin capsules at an average weight of 500 mg. using an MG-2 automatic capsule filling machine.

Examples 8–9 below are also illustrative of mucosal-tenacious vehicles, with a synergistic composition incorporated therein, which can be used in accordance with the teachings of the present invention.

EXAMPLE 8

| Components | % By Weight |
|---|---|
| 1. CMC 7H3SXF (Sodium Carboxymethylcellulose) | 10 |
| 2. Polyox WSR 301 (polyethylene oxide) | 15 |
| 3. Polycarbophil | 15 |
| 4. Calcium Oxide | 1 |
| 5. Ibuprofen | 1 |
| 6. Beta-carotene | 1 |
| 7. Polyvinyl acetate | 23 |
| 8. Triacetin | 34 |
| | 100.0 |

Polyvinyl acetate and triacetin were pre-mixed in a Sigma-blade mixer. CMC7H3SXF, Polyox powder, polycarbophil, calcium oxide and ibuprofen were homogeneously mixed in a Tekman mixer, followed by the addition of Beta-carotene at 1000 rpm. Finally, a polyvinyl acetate/triacetin pre-mix was added to the mixture, and resulted in a smooth cream-type product.

EXAMPLE 9

| Components | % By Weight |
|---|---|
| 1. Ethylene Oxide Homopolymer | 41.0 |
| 2. Polyvinylpyrrolidone | 40.0 |
| 3. Polyethylene Glycol 4000 | 14.9 |
| 4. Glycerin | 1.0 |
| 5. Ibuprofen | 2.0 |
| 6. Beta-carotene | 1.0 |
| 7. Flavor | 0.1 |
| | 100.0 |

The first four ingredients are homogenized into an intimate mixture and warmed to about 40° C. The active agents and flavor were incorporated into the mixture and mixed thoroughly. The final mixture was cooled to about 25° C. and then extruded through stainless steel rollers into a film approximately 2 mm thick.

Although the present invention has been described in connection with preferred embodiments thereof, many other variations and modifications will now become apparent to those skilled in the art without departing from the scope of the invention.

What is claimed is:

1. A method for the treatment of periodontal disease comprising topically administering an effective periodontal disease reducing amount of a composition comprising a synergistic combination of alpha-tocopherol and ketoprofen or a pharmaceutically acceptable salt thereof in a pharmaceutically acceptable carrier to a host in need thereof, wherein the effective periodontal disease reducing amount of the alpha-tocopherol is from about 0.01 to 10% by weight and the effective periodontal disease reducing amount of the ketoprofen is from about 0.01 to 10% by weight, and wherein the amount of alpha-tocopherol is sufficient to lower the $IC_{50}$ value of the ketoprofen and the amount of ketoprofen is sufficient to reduce the $IC_{50}$ value of alpha-tocopherol, and wherein the carrier is a semi-solid paste, gel, liquid, ointment or film which has a strong and continuing adherence to the oral gingival mucosa.

2. A method as claimed in claim 1, wherein the carrier comprises a water soluble or water dispersible polymer.

3. A method as claimed in claim 2, wherein the polymer is selected from the group consisting of karaya gum, ethyleneoxide polymer, sodium carboxymethylcellulose and lower alkyl vinyl ether-maleic acid anhydride copolymer.

4. A synergistic composition for the treatment of periodontal disease comprising an effective periodontal disease reducing amount of alpha-tocopherol and ketoprofen or a pharmaceutically acceptable salt thereof in combination with a topical pharmaceutically acceptable carrier wherein the effective periodontal disease reducing amount of the alpha-tocopherol is from about 0.01 to 10% by weight and the effective periodontal disease reducing amount of the ketoprofen is from about 0.01 to 10% by weight, and wherein the amount of alpha-tocopherol is sufficient to lower the $IC_{50}$ value of the ketoprofen and the amount of ketoprofen is sufficient to reduce the $IC_{50}$ value of alpha-tocopherol, and wherein the carrier is a semi-solid paste, gel, liquid, ointment or film which has a strong and continuing adherence to the oral gingival mucosa.

5. A composition as claimed in claim 4, wherein the effective periodontal disease reducing amount of the alpha-tocopherol is from about 0.03 to 2.0% by weight and the effective periodontal disease reducing amount of the ketoprofen is from about 0.01 to 2% by weight.

6. A composition as claimed in claim 4, wherein the carrier comprises a water soluble or water dispersible polymer.

7. A composition as claimed in claim 6, wherein the combination of the composition and the carrier comprises about 0.01 to 10 parts alpha-tocopherol, and about 0.01 to 10 parts ketoprofen and about 20 to 60 parts polymer.

8. A composition as claimed in claim 7, wherein the polymer is selected from the group consisting of karaya gum, ethyleneoxide polymer, sodium carboxymethylcellulose and lower alkyl vinyl ethermaleic acid anhydride copolymer.

9. A composition as claimed in claim 4 comprising alpha-tocopherol and ketoprofen in a creme carrier comprising a polyacrylic acid polymer.

10. A composition as claimed in claim 1 in which the composition comprises alpha-tocopherol and ketoprofen in a creme carrier comprising a polymacrylic acid copolymer.

11. A method as claimed in claim 1 wherein the effective periodontal disease reducing amount of the alpha-tocopherol is from about 0.03 to 2.0% by weight and the effective periodontal disease reducing amount of the ketoprofen is from about 0.01 to 2% by weight.

12. A method as claimed in claim 2 wherein the combination of the composition and the carrier comprises about 0.01 to 10 parts alpha-tocopherol, and about 0.01 to 10 parts ketoprofen and about 20 to 60 parts polymer.

* * * * *